United States Patent [19]

Moriya

[11] Patent Number: 5,471,298
[45] Date of Patent: Nov. 28, 1995

[54] METHOD AND APPARATUS FOR MEASURING SIZE OF PARTICLE OR DEFECT

[75] Inventor: Kazuo Moriya, Ageo, Japan

[73] Assignee: Mitsui Minings & Melting Co., Ltd., Tokyo, Japan

[21] Appl. No.: 36,986

[22] Filed: Mar. 25, 1993

[30] Foreign Application Priority Data

Mar. 27, 1992 [JP] Japan ................... 4-071593

[51] Int. Cl.⁶ ................... G01N 15/02; G01N 21/53
[52] U.S. Cl. ................... 356/336; 356/339; 356/338; 250/574; 250/222.2; 250/559.45
[58] Field of Search ................... 356/335, 336, 356/338, 339, 341, 364, 369, 367; 250/574, 572, 222.2, 225

[56] References Cited

U.S. PATENT DOCUMENTS

| | | | |
|---|---|---|---|
| 3,869,208 | 3/1975 | Lorenz | 356/336 |
| 4,636,075 | 1/1987 | Knollenberg | 356/336 |
| 4,676,641 | 6/1987 | Bott | 356/336 |
| 4,679,939 | 7/1987 | Curry et al. | 356/339 |
| 4,740,079 | 4/1988 | Koizumi et al. | 356/237 |
| 4,854,705 | 8/1989 | Bachalo | 356/336 |
| 4,952,226 | 8/1990 | Frazee, Jr. et al. | 356/73.1 |
| 4,957,526 | 9/1990 | Frazee, Jr. et al. | 356/73.1 |
| 5,037,202 | 8/1991 | Batchelder et al. | 356/336 |
| 5,256,886 | 10/1993 | Wolf et al. | 356/338 |

FOREIGN PATENT DOCUMENTS

| | | |
|---|---|---|
| 0319797 | 12/1987 | European Pat. Off. . |
| 0391256 | 3/1990 | European Pat. Off. . |
| 151243 | 6/1989 | Japan . |

OTHER PUBLICATIONS

Patent Abstracts of Japan, vol. 14, No. 512, Nov. 1990, "Photoelectric Smoke Sensor".
Patent Abstracts of Japan, vol. 13, No. 413, Sep. 1989, "Measurement of Defect Distribution and Apparatus Therefor".

Primary Examiner—Robert P. Limanek
Assistant Examiner—Alexander Oscar Williams
Attorney, Agent, or Firm—Dorn, McEachran, Jambor & Keating

[57] ABSTRACT

A size of particle or defect in an object is measured. A laser beam is guided through an optical system into the object. A light receiving element receives scattered light from a particle or a defect in the object. A scattering image is formed by an image processor from the scattered light thus received. The size of particle or defect is obtained by integrating a scattering intensity of the scattered light. Also, a size distribution of particle or defect in an object may be acquired by detecting a maximum scattering intensity of each particle or defect. A polarization dependency of scattering may be checked as well.

12 Claims, 11 Drawing Sheets

FIG. 9A (MINUTE PARTICLE SIZE)
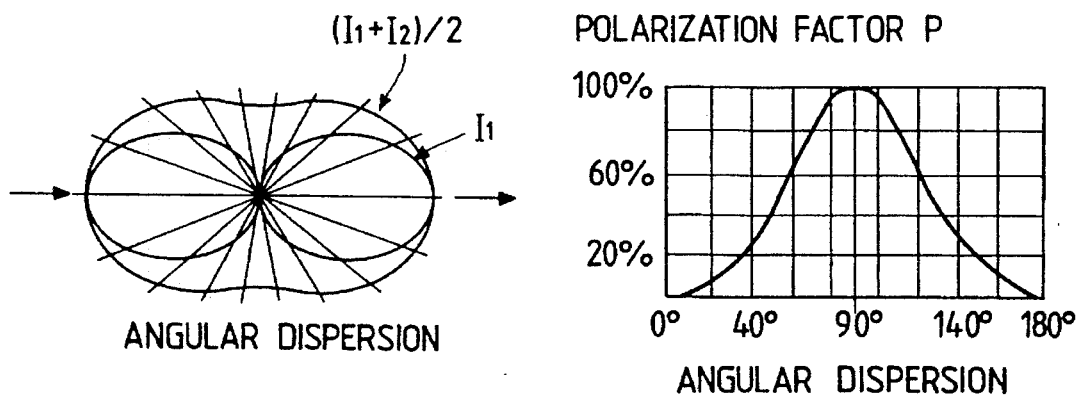
FIG. 9B (PARTICLE SIZE OF 160nm)
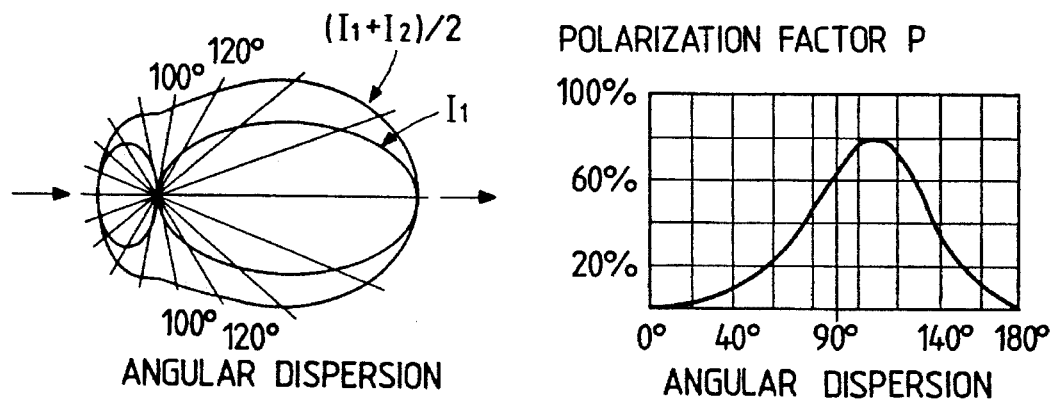
FIG. 9C (PARTICLE SIZE OF 180nm)
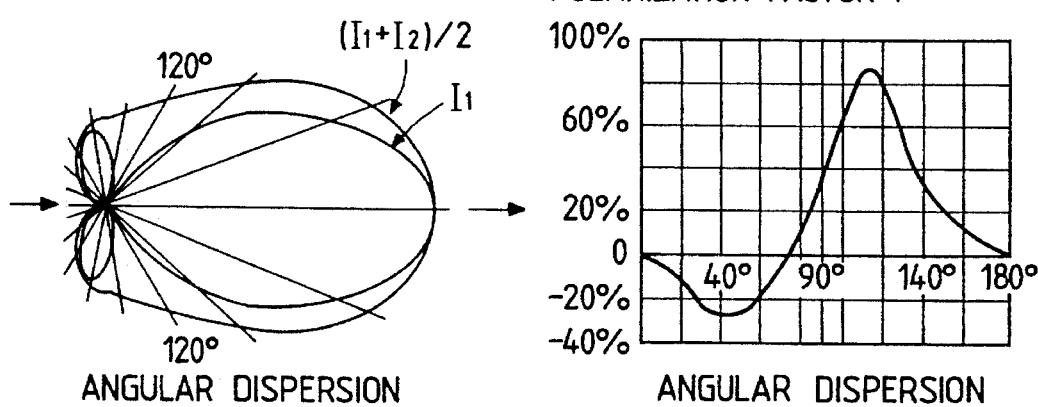

FIG. 11A (DEFOCUSSING STATE)
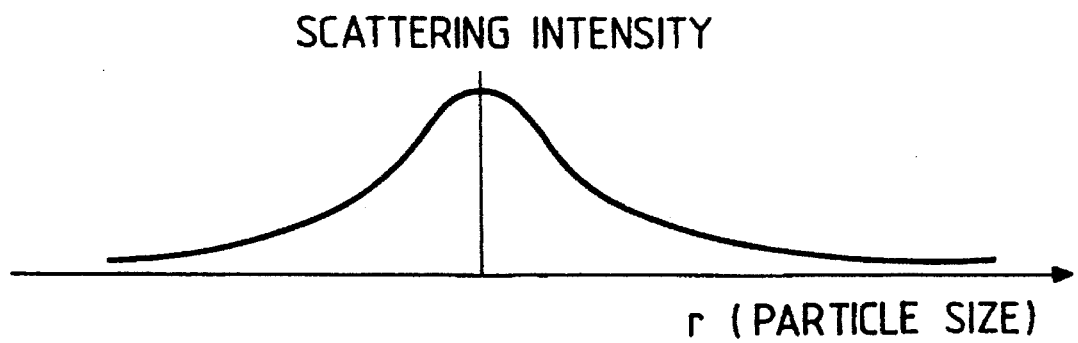
FIG. 11B (JUST FOCUSSING STATE)
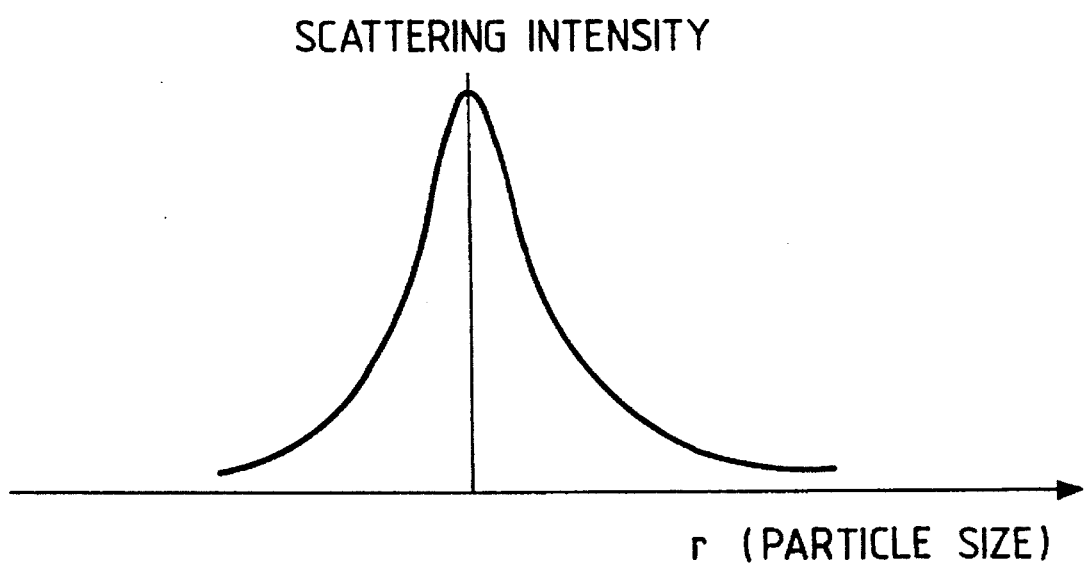

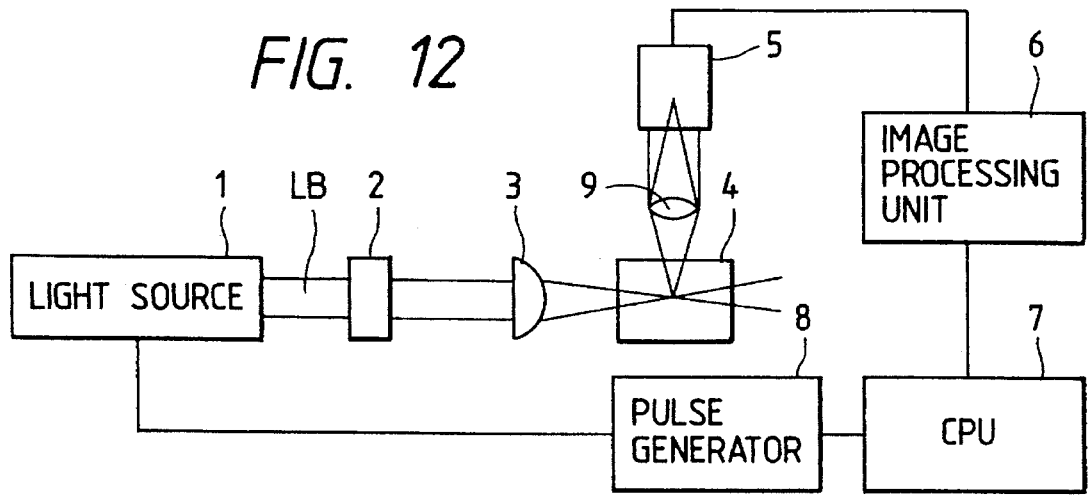

METHOD AND APPARATUS FOR MEASURING SIZE OF PARTICLE OR DEFECT

BACKGROUND OF THE INVENTION

1. Field of the Invention

The present invention relates to a method and an apparatus for obtaining information on a size of particle or defect by measuring light scattered by the particle or defect in a crystal.

2. Related Background Art

There is a conventional method for measuring a distribution of defects in a crystal, as disclosed in Japanese Laid-open Patent Application No. 1-151243, in which a laser beam finely converged is projected into an object, in which image information is obtained of scattered light from defects in the object under irradiation with the laser beam, and in which a density distribution of defects is obtained by processing the image information. A scattering image for example as shown in FIG. 10 may be acquired through this method. Further, a dust counter (employing a laser scattering method) is used for detection of dust existing in liquid or in air, which pulse-counts scattered light from the dust under irradiation with a laser beam. There is also a method known to obtain a particle size distribution, using an angular dispersion of optical scattering from particles.

Using the method as described in Japanese Laid-open Patent Application No. 1-151243, an image may show a size of each particle, as shown in FIG. 10. However, if a size of particle is below one tenth of wavelength of laser beam, an image would have unsharpness or ambiguity due to halation, which makes it difficult to judge a size of particle from the size as shown in the image. Also, the image size of particle may differ depending upon a focus condition of an optical system used, as shown in FIG. 11A and FIG. 11B, which also makes it difficult to obtain accurate information about the size of particle.

The conventional laser scattering methods have a detection limit of about 0.1 μm, so that a particle smaller than the detection limit cannot be detected by the methods. A plurality of fine dust particles present in a laser beam cannot be resolved in the conventional methods, limiting an improvement in detection accuracy.

When the angular dispersion method is employed to obtain the particle size, using the angular dispersion of scattered light intensity, no dispersion is observed from particles with a particle size of about one tenth of beam wavelength, failing to obtain the particle size.

In the measurement of particle size using the angular dispersion of scattered light intensity, it is normally presumed that particles have structures and sizes similar to each other. Thus, the angular dispersion method is not suitable for measurement of a sample in which particles are distributed in a range of several times to about ten times in size. In case that particle sizes are distributed in a broad range, small particles are behind large particles to become undetectable, because the scattering intensity is proportional to the sixth power of particle size.

SUMMARY OF THE INVENTION

As described above, the conventional methods did not permit one to obtain accurate information about size of particle or defect if it has a size of one tenth of wavelength of laser beam used.

It is, therefore, an object of the present invention to provide a method and an apparatus for obtaining information about size of particle or defect with a laser beam being projected into a sample to observe scattered light from the sample, which can provide accurate size information of defect or particle even if the defect or particle in the sample has a size of about one tenth of wavelength of the laser beam. It is a further object of the present invention to provide a method or an apparatus for obtaining size information of particle or defect independent of a focus condition of an optical system used therein.

It is a still further object of the present invention to provide a method and an apparatus for obtaining size information of particle or defect, which permits a measurement of a sample in which particles or defects to be measured have small to large sizes distributed in a wide range.

A method or an apparatus according to the present invention, achieving the above objects, is characterized to have steps or means of: radiating a laser beam toward a sample to be measured; receiving scattered light produced by a particle or defect in a direction intersecting with an optical path of the radiated beam; integrating an intensity of scattered light thus received; and then obtaining size information of the particle or defect, based on the integrated intensity of the scattered light.

As described above, a size of particle observed in an image differs depending upon a focus condition of an optical system used, but the integrated intensity of scattered light can be considered as constant. Then, if the integrated intensity of scattered light is first obtained and if the size information of particle is then obtained based on the integrated intensity, accurate information may be attained about the size of particle irrespective of focus condition.

Further, in the present invention, a step or means may be provided for obtaining a maximum value of the scattered light intensity received, whereby information may be obtained about a relative size of particle or defect.

Additionally, in the present invention, a step or means may be provided for measuring a polarization dependency of scattering by a particle or defect, whereby accurate information may be obtained about the size and the structure of particle or defect.

BRIEF DESCRIPTION OF THE DRAWINGS

FIG. 9A is a drawing to show an angle dependency of scattering caused by a particle having a predetermined size, specifically showing an angular dispersion of scattering and an angular dispersion of the degree of polarization P when the particle is minute;

FIG. 9B is a drawing to show an angle dependency of scattering caused by a particle having a predetermined size, specifically showing an angular dispersion of scattering and an angular dispersion of the degree of polarization P when the particle has a diameter of 160 nm;

FIG. 9C is a drawing to show an angle dependency of scattering caused by a particle having a predetermined size, specifically showing an angular dispersion of scattering and an angular dispersion of the degree of polarization P when the particle has a diameter of 180 nm;

FIG. 11A is a scattering intensity distribution, which was obtained in a defocus (out-of-focus) condition of an optical system in the apparatus;

FIG. 11B is a scattering intensity distribution, which was obtained in a just focus (in-focus) condition of the optical system in the apparatus;

FIG. 12 is a constitutional drawing to show a further embodiment of the apparatus according to the present invention;

FIG. 13 is an explanatory drawing to show steps for obtaining a maximum scattering intensity from image data of an image processor 6, in which a peak point represents a pixel showing the maximum scattering intensity and pixels adjacent to the pixel are given numbers in order;

DETAILED DESCRIPTION OF THE PREFERRED EMBODIMENTS

The preferred embodiments according to the present invention will be described in detail with reference to the accompanying drawings.

Figure 1:
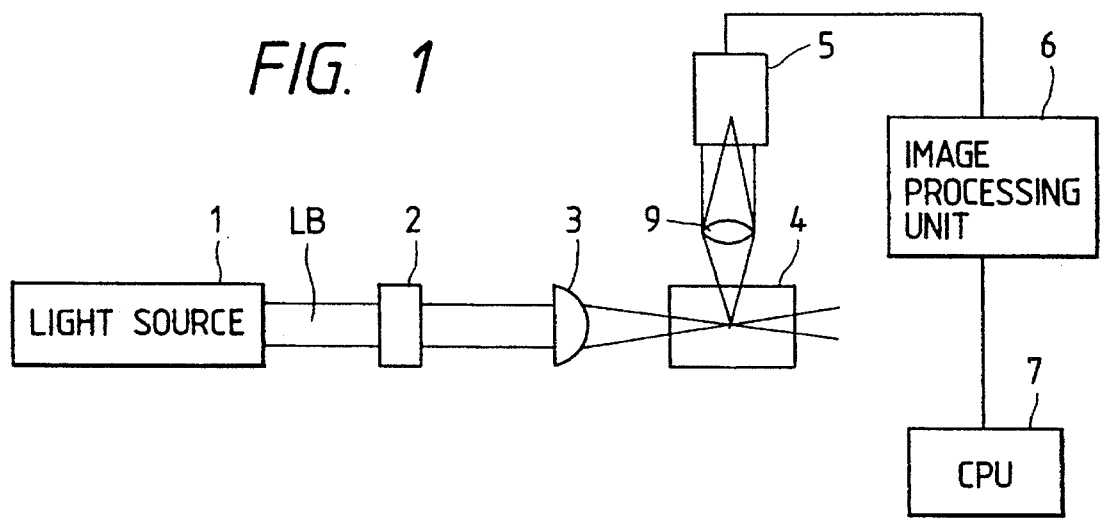
FIG. 1 is a drawing to show a structure of an apparatus as an embodiment according to the present invention.

FIG. 1 shows an apparatus for obtaining information about a size of defect or particle (as will be referred to simply as "particle"), according to the present invention. In FIG. 1, reference numeral 1 designates a light source for radiating a laser beam LB. The radiated laser beam is converted into a parallel beam through a cylindrical lens 2, and the parallel beam is condensed through a spherical lens 3 to irradiate a sample 4 with the beam shaped in a linear section. Although the sample 4 is irradiated with the linear beam in the present embodiment, the irradiation beam is not limited to the linear beam. For example, the sample 4 may be irradiated with a normally condensed beam (spot beam). When the linear beam is incident into the sample 4 as described, scattering is caused by particles in the sample, and an image pickup device 5 receives through an optical system 9 light scattered in a direction intersecting with an optical path of the incident beam into the sample 4. The received light is processed by an image processing unit 6 to obtain an image of particles. The thus-obtained image is processed by a CPU 7, which executes integration of scattering intensity for each particle by the following method. Each particle has a spread of scattering. A radius vector function is obtained to define the spread of scattering and a function of unsharpness or ambiguity f(x) is also obtained. The integration is carried out within a certain radius defined for each particle. The function of ambiguity depends upon a shape of scattering body.

For example;

in case of a sphere, $$f(r) = \{\sin(ka)/(ka)\}^2;$$

in case of a plate, $$f(r) = \{3(ka)^3 \times [\sin(ka) - (ka)\sin(ka)]\}^2.$$

Note that k is a proportion constant. These are obtained from the equations of light diffraction. Further, the scattering intensity is proportional to the sixth power of diameter of particle, so that a size of each particle may be calculated based on the integral intensity of scattered light. The CPU 7 executes the integration of integral intensity of scattered light and the calculation of size of particle as described.

Specifically, the integration of scattering intensity distribution is carried out as follows.

Figure 2:
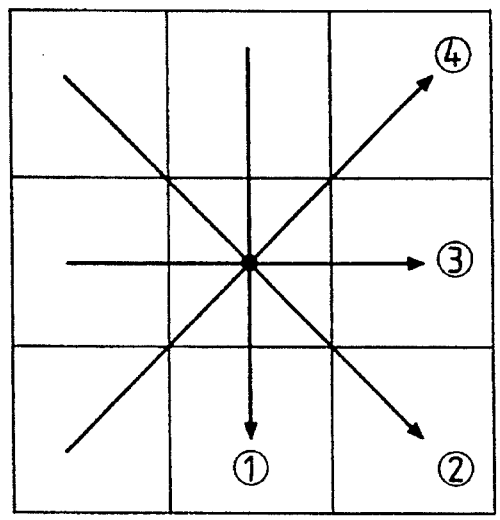
FIG. 2 is an explanatory drawing to show a method for obtaining a peak while scanning in the four directions of arrows an area in a scattering image including a center pixel and adjacent eight pixels, using the apparatus in the embodiment according to the present invention.
Figure 14:
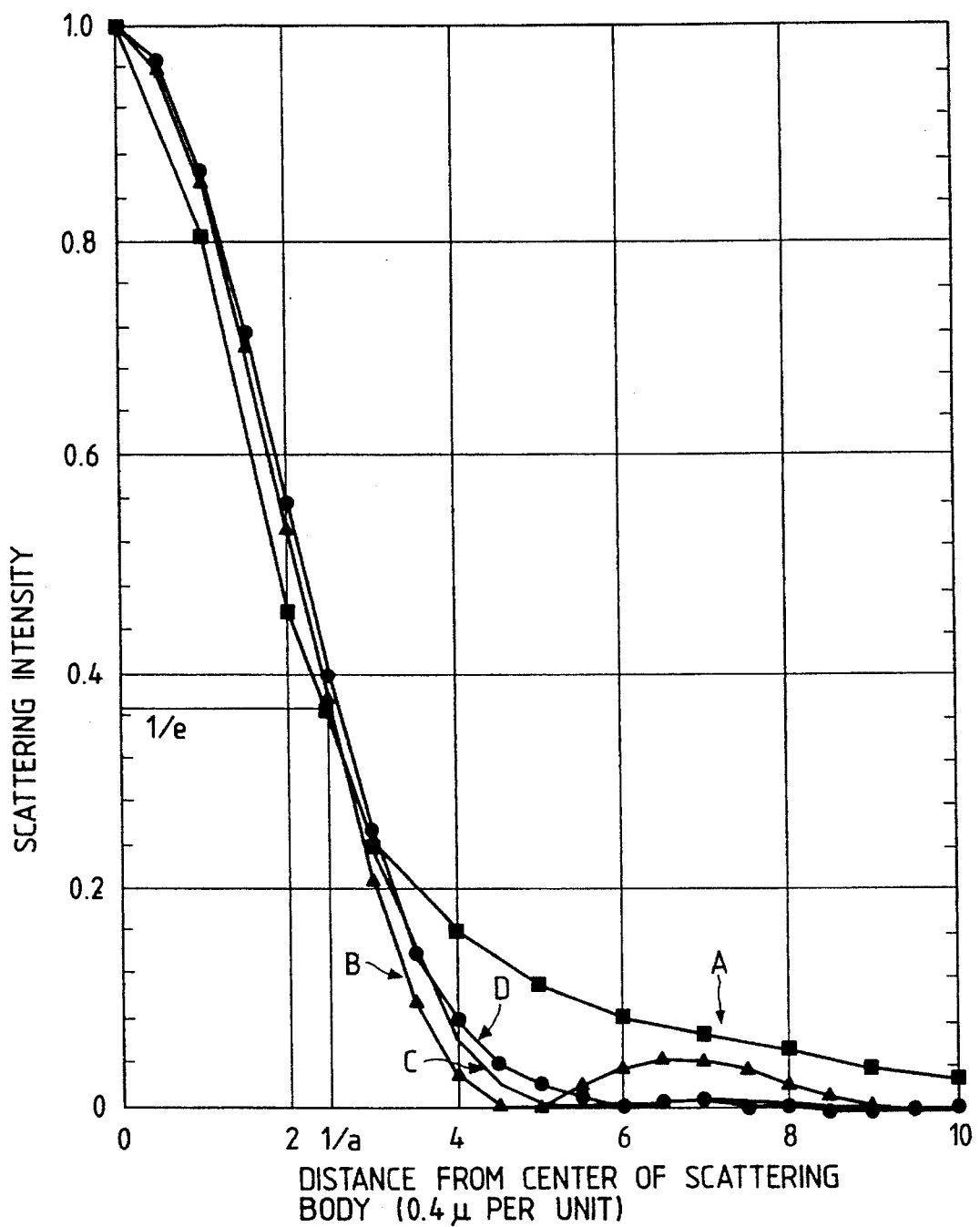
FIG. 14 is a plotted drawing to show a relation between a scattering intensity and a distance from the center of scattering body, in which A represents a distribution function (measured value) obtained from a scattering body, B and C theoretical scattering intensity distribution functions of a plate scattering body and of a spherical scattering body, respectively, and D a Gaussian distribution function.

The scattering integral intensity I may be expressed as follows.

$$I = \int I_P f(r) 2\pi r \, dr = 2\pi I_P \int r f(r) \, dr,$$

where $I_P$ is a maximum scattering intensity and r a radius vector. A search of ① to ④ as shown in FIG. 2 is conducted on image data output from the image processor 6 to obtain the maximum scattering intensity by a method as described later. Then, a scattering intensity is obtained for each pixel, one for first proximate pixel, another for second proximate pixel, ..., another for n-th proximate pixel around the peak point (maximum scattering intensity), as shown in FIG. 13. Plotting a relation between the scattering intensity and the distance from the scattering body center, the scattering intensity distribution of a particle is obtained as a distribution function as shown by A in FIG. 14. FIG. 14 also shows a scattering intensity distribution B of a plate scattering body and a scattering intensity distribution C of a spherical scattering body calculated from the above ambiguity function. These distribution functions assure that the distribution function f(r) can be approximated to a Gaussian distribution D.

Thus, if the distribution function is approximated as $f(r)=\exp(-ar^2)$, the integration may be carried out as follows:

$$\int 2\pi r f(r) dr = \pi/a.$$

Figure 15:
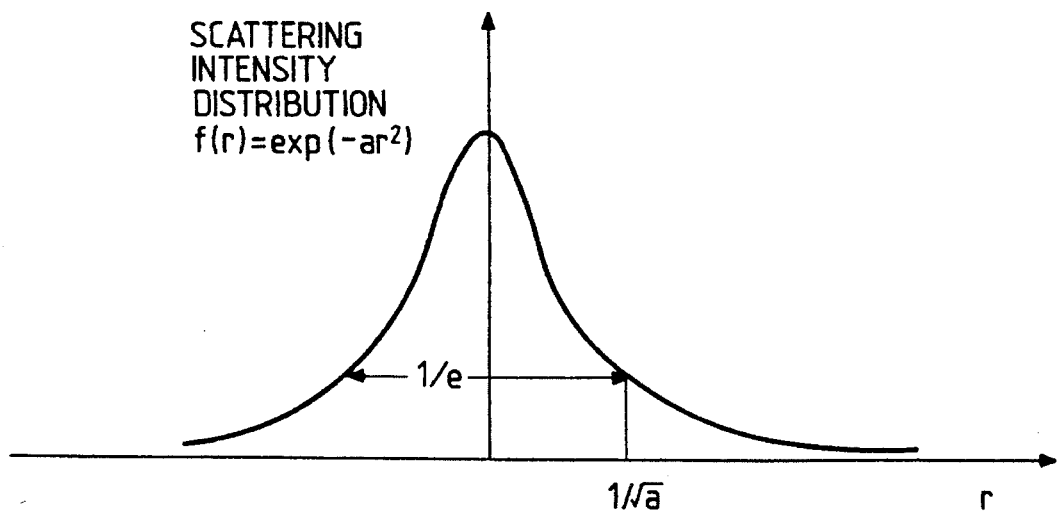
FIG. 15 shows an approximate scattering intensity distribution.

Thus, the scattering integral intensity I may be expressed as $I=(\pi/a)I_P$. The scattering intensity distribution may be as shown in FIG. 15. As shown in FIG. 15, a half-width $1/\sqrt{a}$ is a radius where the function f(r) takes the value of 1/e. Thus, if a radial distribution of scattering intensity is gained for a pixel having the maximum scattering intensity and if a distance where the function takes the value 1/e is obtained, an accurate integral intensity may be steadily attained by multiplying a peak intensity in scattering intensity by a square of the obtained distance.

The radius $1/\sqrt{a}$ may be uniquely determined as in the above description. However, since the value of radius differs depending upon the focusing condition of the optical system used, the radius $1/\sqrt{a}$ may be determined such that scattering intensities are obtained for some pixels, that a distribution function f(r) is obtained from the scattering intensities, and that a radius where the function f(r) takes the value 1/e is then obtained.

Next explained with FIG. 12 is an embodiment in which information is obtained about a size of particle moving in liquid or in gas.

In FIG. 12, numeral 1 designates a light source for radiating a pulse laser, which radiates a pulse laser beam in accordance with a signal generated by a pulse generator 8 when it receives a command from a CPU 7. A pulse width (time) is determined such that a product of the pulse width with the maximum velocity ($V_{MAX}$) of particle is fully smaller than a space resolving power of measurement. Provided that a velocity is V, that a pulse width is τ, and that the maximum speed of particle $V_{MAX}$ is equal to $10^4$ μsec, the pulse width τ would be $10^{-4}$ to $10^{-5}$ sec. The emission of pulse laser must be synchronized with reception of scattering image. In detail, the CPU 7 executes such a control that a scattering image is received after emission of pulse. The pulse laser beam is made parallel through a cylindrical lens 2, and the parallel beam is shaped into a linear section through a spherical lens 3 then to enter a cell of liquid or gas. An image pickup device 5 receives through an optical system 9 light scattered in a direction intersecting with the incident light path, to obtain a stationary image. A scattering integral intensity is obtained as described above, based on the stationary image, whereby the size information of particle and a particle distribution may be obtained.

Next explained is a method for obtaining a maximum value of scattering intensity and then obtaining information of relative size of particle from the maximum value.

Figure 3:
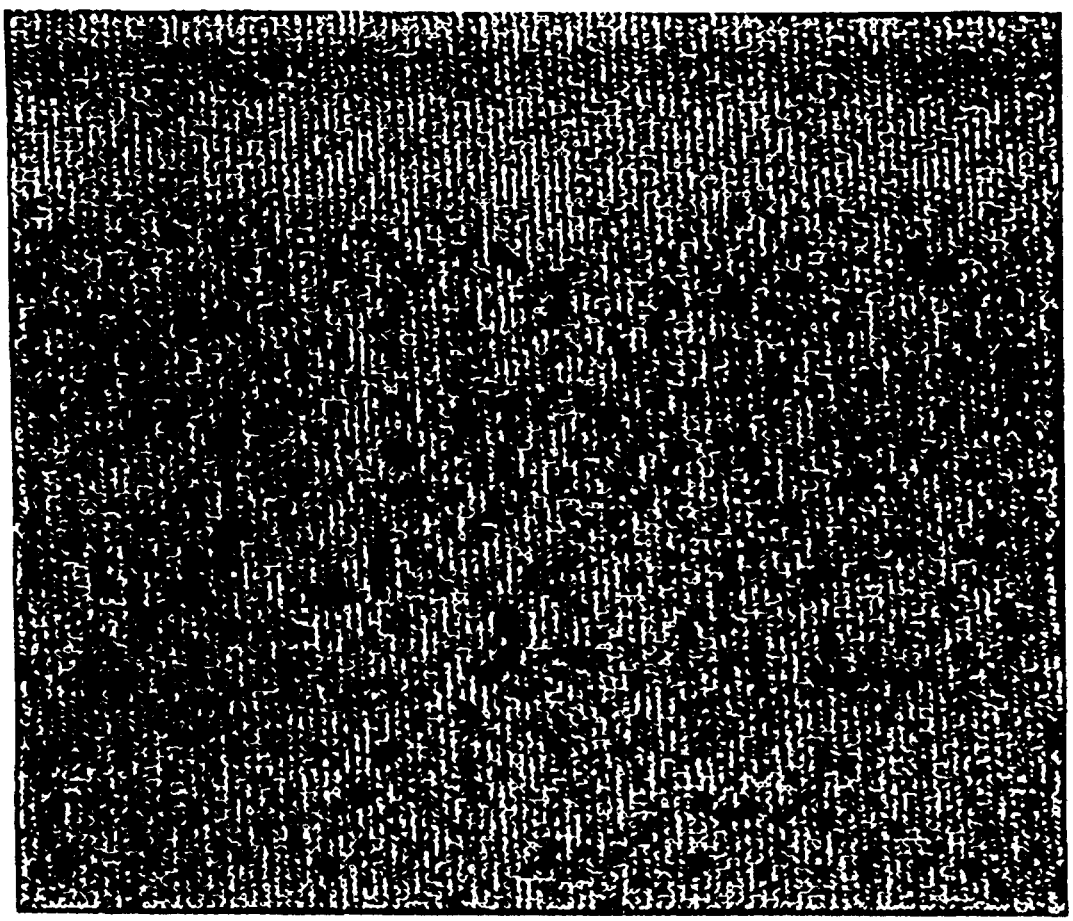
FIG. 3 is a drawing to show a scattering image of defects after image-processed.
Figure 4:
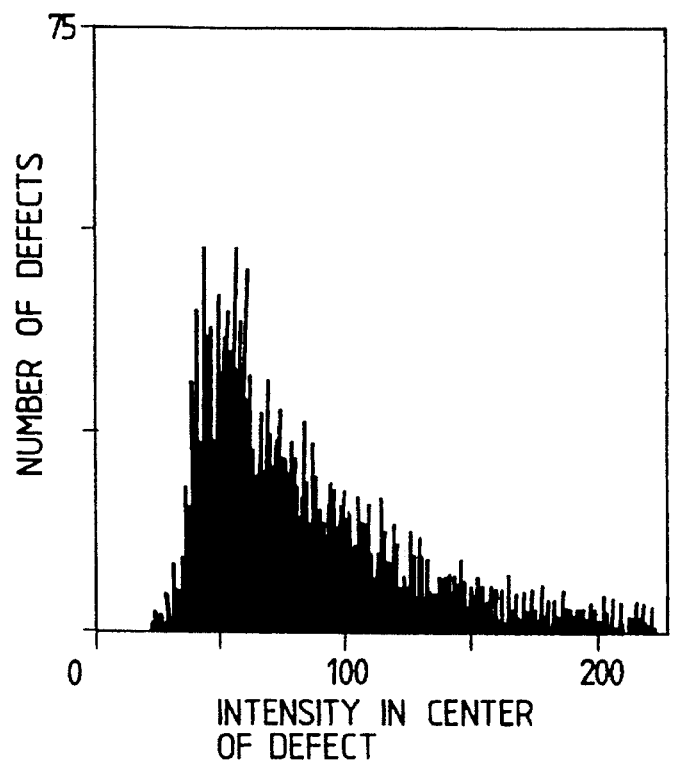
FIG. 4 is a graph to show a relation between a scattering intensity at a scattering center of each defect, which is shown on the horizontal axis, and a number of defects which is on the vertical axis in the scattering image as shown in FIG. 3.

In the apparatus as shown in FIG. 1, the image processor 6 searches a maximum value of scattering intensity in an area including a pixel and eight pixels surrounding the pixel on a scattering image obtained by the image pickup device 5 in the four directions as shown by the arrows in FIG. 2. This operation is carried out for all pixels. FIG. 4 is a graph obtained by seeking a value of scattering intensity at a peak position (maximum scattering intensity) for each defect by the above described method on the scattering image of FIG. 3 (in which dark portions correspond to defects). In FIG. 4, the horizontal axis represents a scattering intensity at the center of each defect (at the scattering intensity peak position) and the vertical axis a number of defects. It is seen from FIG. 4 that defects with a center intensity of about 50 are the majority of the plural defects as shown in FIG. 3.

Figure 5:
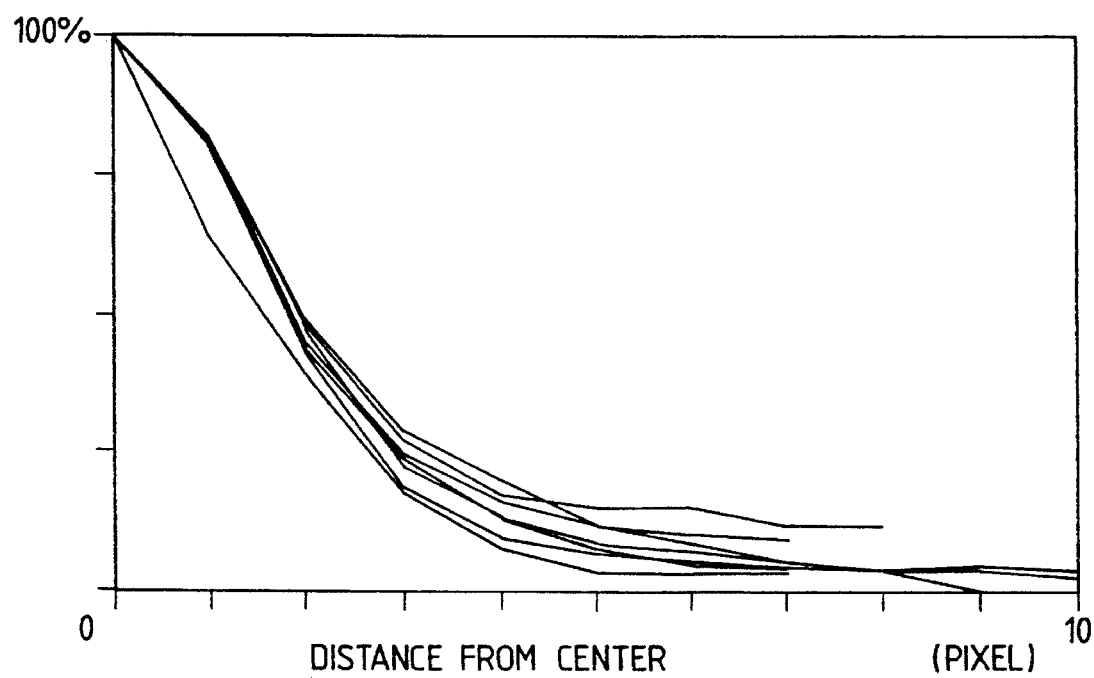
FIG. 5 is a graph to show a distribution of scattering intensity in a direction of radius vector, in which the scattering intensity at the center of defect is set as 1 and the each scattering intensity in the direction of radius vector is normalized, where the vertical axis represents the normalized scattering intensity, the horizontal axis a distance from the center of scattering body, in the unit of pixel, each pixel being 0.4 μm.

FIG. 5 shows plots of scattered light intensity distributions in the direction of radius vector obtained from several defects different in center intensity of defect, which are normalized with the center scattering intensity of each defect being 100%. It is understood from this graph that the scattering intensity distributions have almost the same shape in the direction of radius vector from the defect center even if the defect center intensity varies 50 to 100. Thus, once the maximum scattering intensity of each defect is obtained, information may be obtained about a size of defect. In detail, an integral scattering intensity I of each defect may be expressed as follows if the radius vector is vector r and the scattering intensity of each pixel is i.

$$I=\int i(r)dr \qquad (1)$$

Since the distribution function f(r) of scattering intensity is independent of the scattering intensity $I_P$ at a peak position thereof, the integral scattering intensity may be expressed as follows.

$$I=\int i(r)dr = I_P \int f(r)dr = KI_P \qquad (2)$$

where K is a proportion constant.

Accordingly, once the scattering intensity $I_P$ is detected at a peak position thereof, the integral scattering intensity may be calculated. Further, in case that a particle has a size considerably smaller than a wavelength of the laser beam used, the integral scattering intensity may be expressed as follows because the integral scattering intensity is proportional to the sixth power of particle size.

$$I=KI_P=cd^6 \qquad (3)$$

where c is a proportion constant. Calculating the sixth root of the maximum scattering intensity $I_P$ from the equation (3), a relative diameter of particle may be obtained.

In the embodiments according to the present invention, the above calculation is carried out by the CPU 7 in the apparatus as shown in FIG. 1.

Specifically, the maximum scattering intensity may be obtained through the following steps.

Figure 16:
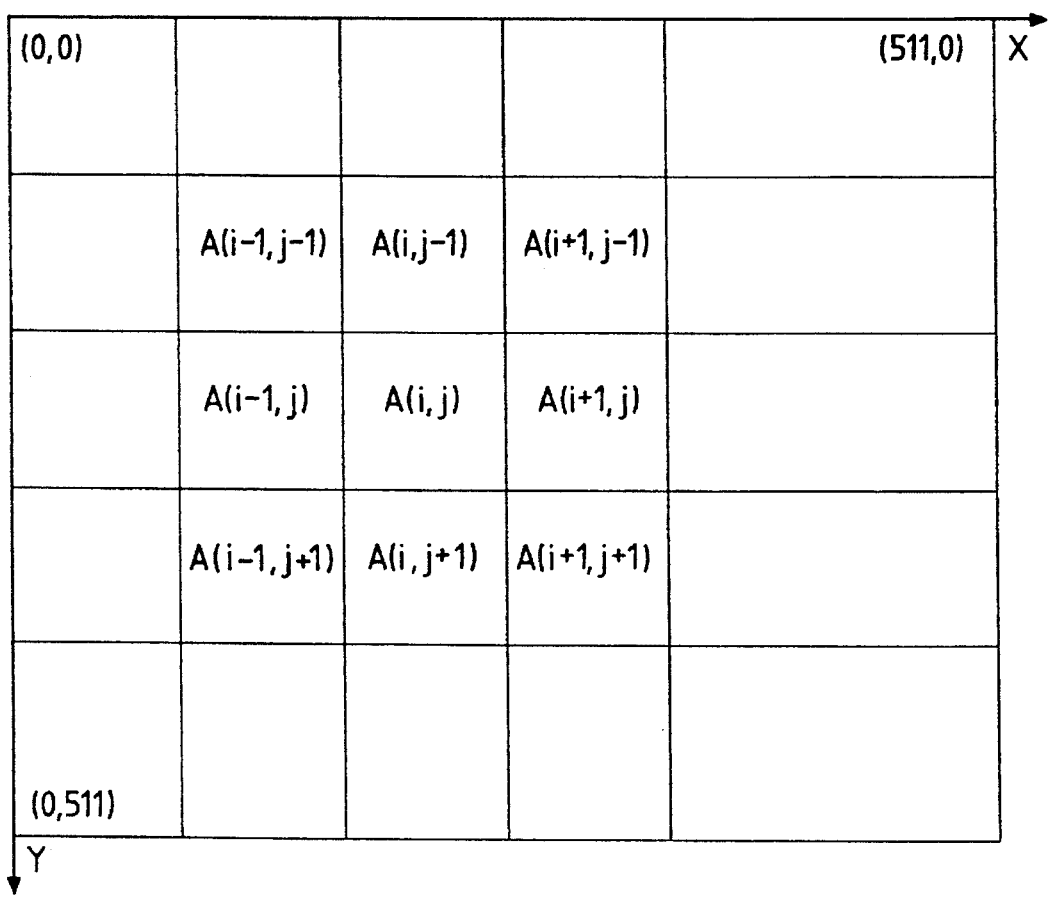
FIG. 16 is an explanatory drawing to illustrate how to obtain a peak point showing the maximum scattering intensity based on image data from the image processor, in which each section in matrix represents a pixel, A a scattering intensity, and characters in parentheses a coordinate location of each pixel.

In image data output from the image processor 6, a maximum scattering intensity is obtained based on scattering intensity of each pixel on a scattering image. For example, as shown in FIG. 16, the following conditions must be satisfied in relation with scattering intensities of adjacent pixels in order that A(i, j) becomes a peak of scattering intensity.

$$A(i-1, j-1) \leq A(i, j) \geq A(i+1, j+1);$$

$$A(i-1, j) \leq A(i, j) \geq A(i+1, j+1);$$

$$A(i-1, j+1) \leq A(i, j) \geq A(i+1, j-1);$$

$$A(i, j+1) \leq A(i, j) \geq A(i, j-1);$$

Obtaining a point (i, j) satisfying the above conditions, the scattering intensity at that point may be selected as the maximum scattering intensity $I_P$ by the CPU. Alternatively, the maximum scattering intensity may be obtained in the image processor as described above.

Also, since the distribution function of scattering intensity varies depending upon a focus condition of an optical system used, distribution functions of scattering intensity may be obtained in sampling of several particles from the peak position showing the maximum of scattering intensity, whereby obtaining a corrected distribution function.

A further embodiment according to the present invention is next explained with reference to FIG. 6.

Figure 6:
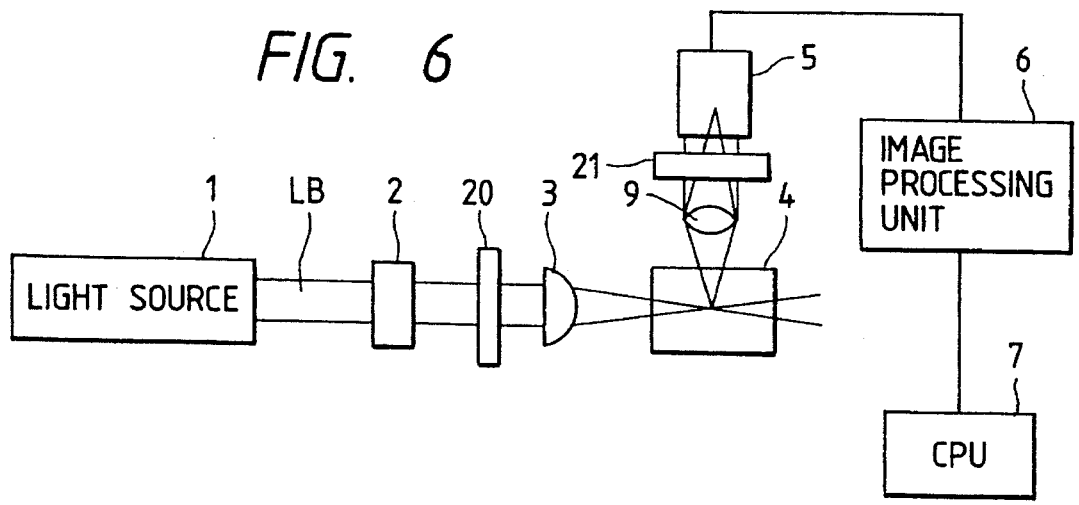
FIG. 6 is a constitutional drawing to show another embodiment of the apparatus according to the present invention.
Figure 7:
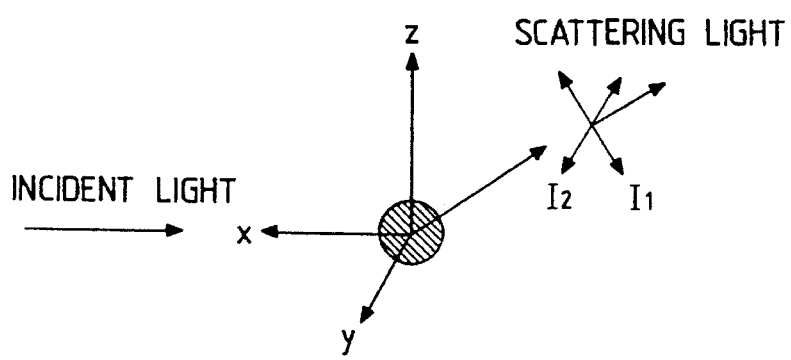
FIG. 7 is a drawing to show a coordinate system of polarization direction with respect to a scattering body.
Figure 8:
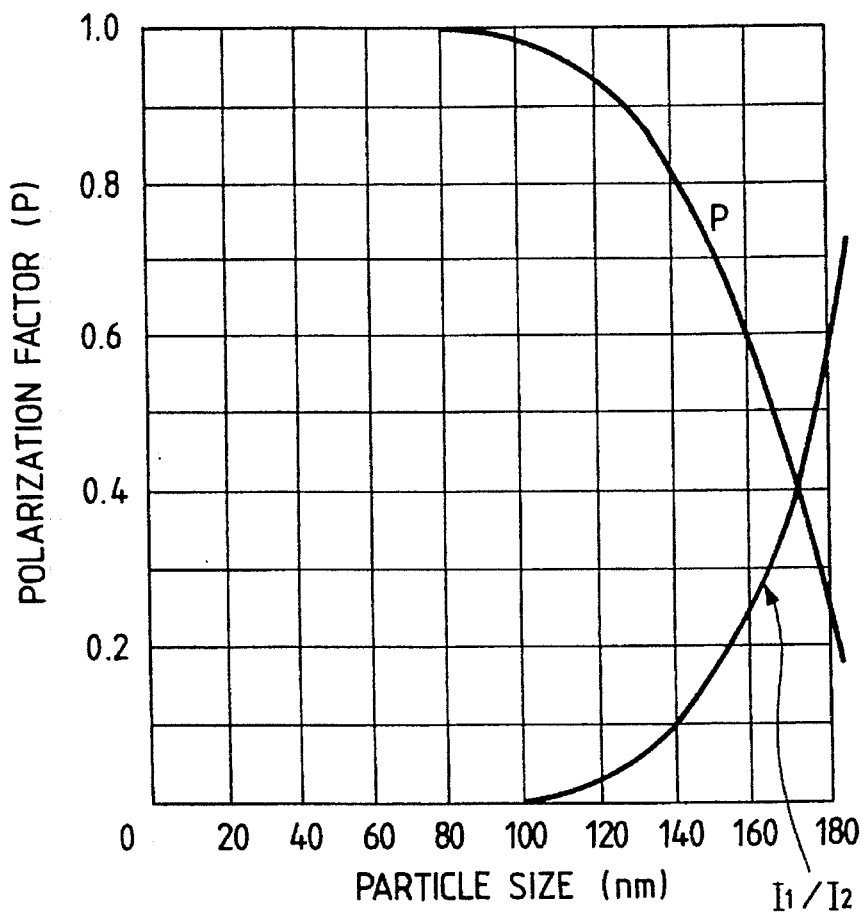
FIG. 8 is a graph to show a relation between a particle size of gold colloid and a degree of polarization P, or $I_1/I_2$, where the horizontal axis represents a particle size and the vertical axis a degree of polarization P.
Figure 10:
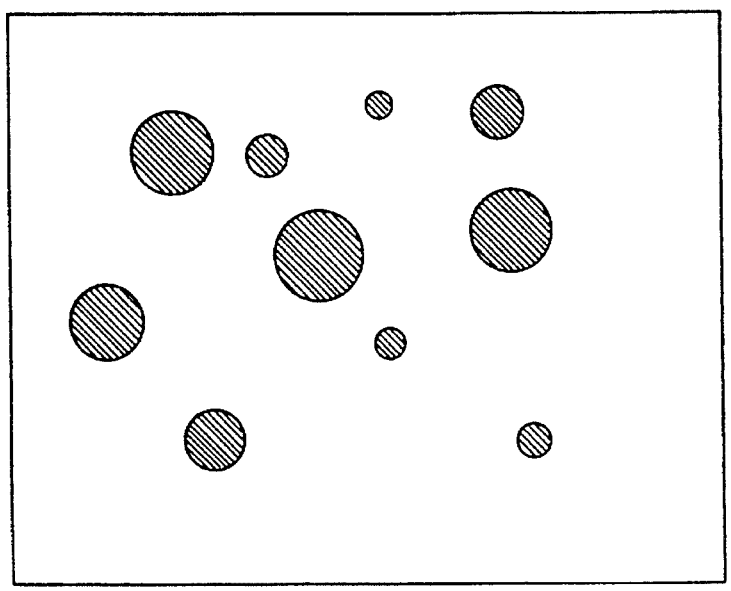
FIG. 10 is a drawing to schematically show a scattering image of particles in the laser scattering method.

In the apparatus as shown in FIG. 6, a polarizing plate 20 is disposed in front of a spherical lens 3, so that the polarizing plate 20 fixes the polarization direction of laser beam in a predetermined direction to guide the laser beam into a sample 4. The same elements are given the same reference numerals as those in the apparatus of FIG. 1, and are omitted to explain here. Further, an analyzer 21 is disposed behind an optical system 9, to measure a degree of polarization in scattering of particle. In detail, setting the x-, the y-, and the z-directions as in the coordinate system as shown in FIG. 7, a composition or a size of particle (scattering body) may be known by measuring for example I(y, x), I(y, y), I(z, x), I(z, Y).

I(y, x) represents a scattering intensity when the incident light is polarized in the y-direction and the scattered light in the x-direction.

For example, in case of gold colloid as the scattering body, a particle size dependency of scattering from gold colloid may be as shown in FIGS. 9A to 9C referring to Mie, Ann, d. Physik (4) 25 (1908) 377. Thus, measuring the degree of polarization P or $I_1/I_2$, the particle size may be obtained uniquely. Here, $I_1$ is a scattering intensity when the incident light and the scattered light both are polarized in parallel with the xz plane, and $I_2$ is a scattering intensity when the incident light and the scattered light both are polarized in the y-direction. The degree of polarization P is expressed as follows.

$$P=(I_2-I_1)/(I_2+I_1)$$

FIG. 9A to FIG. 9C respectively show an angular dispersion of scattering intensity, in which the angular dispersion of scattering differs depending upon the particle size of scattering body. For example, observing the degree of polarization P at 90 degrees of scattering, the degree of polarization P is 60% with a particle of diameter 160 nm, while the degree of polarization P is 30% with a particle of diameter 180 nm.

The degree of polarization P is calculated by the CPU 7 in the present embodiment.

Specifically, the calculation is carried out through the following steps.

Since $I_1$ is the scattering intensity when the incident light and the scattered light both are polarized in parallel with the xz plane, the polarizing elements 20 and 21 are set to obtain $I_1$ in the apparatus of FIG. 6. Similarly, since $I_2$ is the scattering intensity when the incident light and the scattered light both are polarized in the y-direction, the polarizing elements 20 and 21 are set to obtain $I_2$ in the apparatus of FIG. 6. Then, from image data obtained by the image processor 6, the maximum scattering intensity in the polarization direction may be obtained by the above method as $I_1$ or $I_2$. The degree of polarization P can be calculated based on the thus-obtained $I_1$ and $I_2$. Further, size information of particle may be obtained based on the degree of polarization P.

Figure 17:
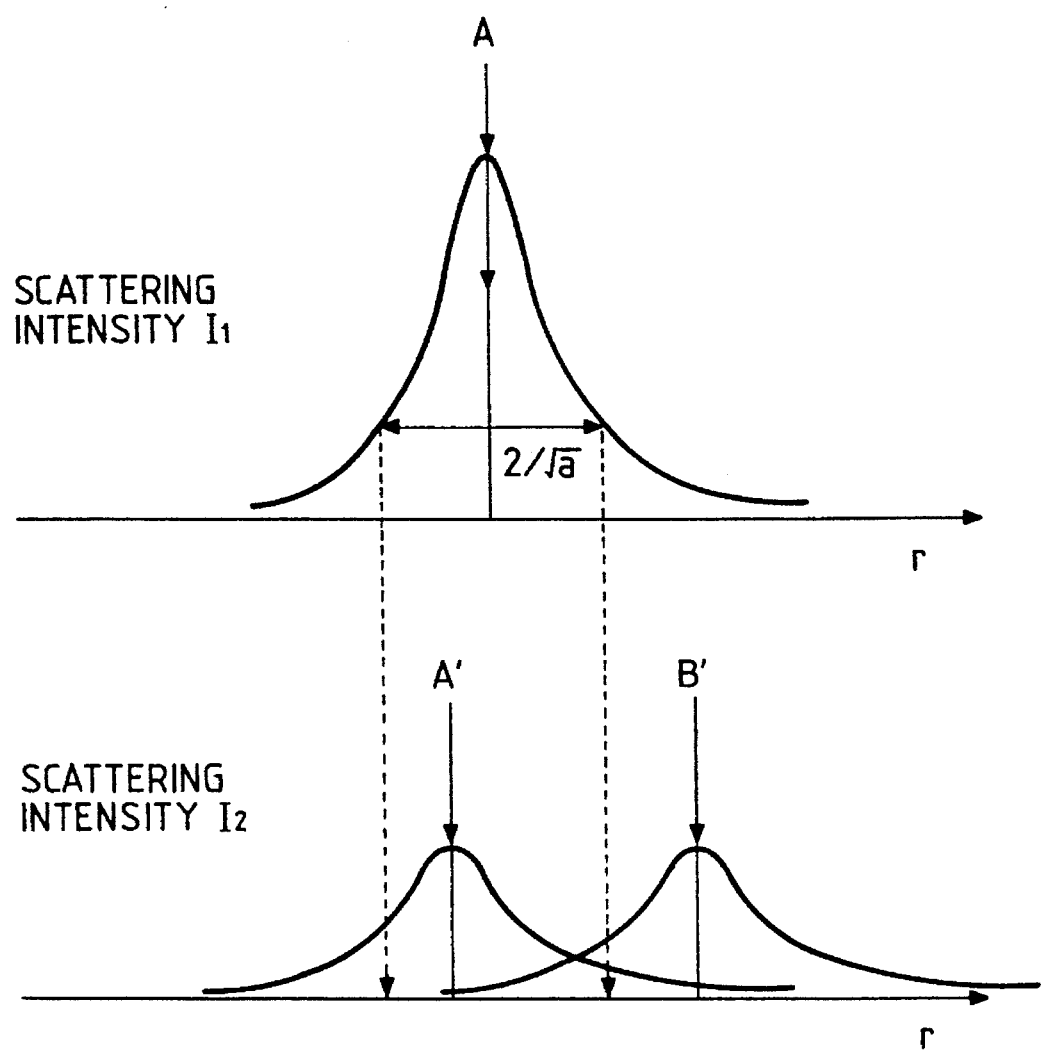
FIG. 17 is a drawing to show a case in which a peak point of scattering intensity $I_1$ is deviated relative to a peak point of scattering intensity $I_2$, and in which the vertical axis represents a scattering intensity and the horizontal axis a radius vector (r).

It is possible as shown in FIG. 17 that a peak point of $I_1$ is deviated relative to a peak point of $I_2$ even with a single particle. In such a case, a corresponding peak point is chosen in a range of ambiguity $(2/\sqrt{a})$ on a scattering image. For example, in FIG. 17, a peak point of the scattering intensity $I_1$ is at point A, but a peak point of the scattering intensity $I_2$ is deviated from the point A. There are two peaks at point A' and at point B' in this example as shown. Since the point B' is out of the range of ambiguity $(2/\sqrt{a})$ of the scattering intensity $I_1$, the degree of polarization P may be obtained determining the point A' as a peak point of the scattering intensity $I_2$ corresponding to the point A.

According to the present invention, individual size information may be obtained with a particle smaller than the diameter of laser beam.

Precipitates in a crystal will have crucial effects on physical properties such as hardness of crystal. Thus, controlling a particle size, a structure, and a density of precipitates, a desired crystal may be obtained. The precipitates are different depending upon raising conditions of crystal or upon conditions of thermal treatment. Therefore, a desired crystal may be obtained by determining the raising conditions of crystal or the conditions of heat treatment, based on the size information of particles or precipitates obtained according to the present invention.

What is claimed is:

1. A method for measuring a size of particle or defect, comprising:

a step of irradiating an object with a laser beam;

a step of receiving scattered light from a particle or defect in said object and image-processing said scattered light received; and a step of integrating a two-dimensional intensity of said scattered light from the particle or defect and determining the size of particle or defect based on the maximum value of the integrated scattered light.

2. A method for measuring a size of particle or defect according to claim 1, further comprising a step of measuring a degree of polarization of said scattered light from the particle or defect.

3. A method according to claim 1, wherein said laser beam is a pulse laser beam, which is projected through an optical system in the shape of linear section on said object to be irradiated therewith.

4. An apparatus for measuring a size of particle or defect in an object, comprising:

a light source for radiating a laser beam;

a first optical system for irradiating an object with said laser beam;

a light receiving element for receiving through a second optical system scattered light from a particle or defect in said object;

means for obtaining a two-dimensional scattering image based on the scattered light detected by said light receiving element; and means for integrating the two-dimensional scattering intensity of said scattered light and for determining the maximum value of the integrated scattered light to obtain a size of the particle or defect.

5. An apparatus according to claim 4, wherein said first optical system comprises a polarizing plate for polarizing the laser beam incident into said object in a predetermined polarization direction, and wherein said second optical system comprises an analyzer for detecting a polarization direction of the scattered light from the particle or defect in said object, further comprising means-for calculating a degree of polarization.

6. An apparatus for measuring a size of particle or defect in an object, comprising:

a light source for radiating a laser beam;

a first optical system for irradiating an object with said laser beam;

a light receiving element for receiving through a second optical system scattered light from a particle or defect in said object; and means for obtaining a two-dimensional intensity of the scattering image based on the scattered light detected by said light receiving element;

wherein a maximum scattering intensity of said two-dimensional scattered light from the particle or defect is detected by said means for obtaining a scattering image.

7. An apparatus according to claim 6, further comprising means for deriving a size distribution of particle or defect in the object from the detected maximum scattering intensity of each particle or defect.

8. An apparatus according to claim 4, wherein said light source is connected to a pulse generator, said light source emitting a pulse laser beam, and wherein said object is irradiated through said first optical system with the pulse laser beam of linear section.

9. A method according to claim 2, wherein said laser beam is a pulse laser beam, which is projected through an optical system in the shape of linear section on said object to be irradiated therewith.

10. An apparatus according to claim 5, wherein said light source is connected to a pulse generator, said light source emitting a pulse laser beam, and wherein said object is irradiated through said first optical system with the pulse laser beam of linear section.

11. An apparatus according to claim 6, wherein said light source is connected to a pulse generator, said light source emitting a pulse laser beam, and wherein said object is irradiated through said first optical system with the pulse laser beam of linear section.

12. An apparatus according to claim 7, wherein said light source is connected to a pulse generator, said light source emitting a pulse laser beam, and wherein said object is irradiated through said first optical system with the pulse laser beam of linear section.

* * * * *